(12) United States Patent
Homeier et al.

(10) Patent No.: US 8,920,422 B2
(45) Date of Patent: Dec. 30, 2014

(54) METHOD FOR TIBIAL NAIL INSERTION

(75) Inventors: Annika Homeier, Kiel (DE); Ilan Howling, Kiel (DE); Nils Zander, Eckernförde (DE); Lothar Kühne, Mielkendorf (DE); Claudia Graca, Kiel (DE)

(73) Assignee: Stryker Trauma GmbH (DE)

( * ) Notice: Subject to any disclaimer, the term of this patent is extended or adjusted under 35 U.S.C. 154(b) by 365 days.

(21) Appl. No.: 13/234,629

(22) Filed: Sep. 16, 2011

(65) Prior Publication Data

US 2013/0072931 A1 Mar. 21, 2013

(51) Int. Cl.
*A61B 17/56* (2006.01)
*A61B 17/72* (2006.01)

(52) U.S. Cl.
CPC ............... *A61B 17/56* (2013.01); *A61B 17/72* (2013.01); *A61B 2017/564* (2013.01)
USPC .......................................................... 606/62

(58) Field of Classification Search
USPC .................................................... 606/62–64
See application file for complete search history.

(56) References Cited

U.S. PATENT DOCUMENTS

| | | | |
|---|---|---|---|
| 2003/0195515 A1* | 10/2003 | Sohngen | 606/62 |
| 2007/0073296 A1* | 3/2007 | Panchbhavi | 606/62 |
| 2007/0123878 A1* | 5/2007 | Shaver et al. | 606/64 |

FOREIGN PATENT DOCUMENTS

WO WO 2009150691 A1 * 12/2009

OTHER PUBLICATIONS

Kevin M. Kahn, MD, et al. "Malrotation After Locked Intramedullary Tibial Nailing: Three Case Reports and Review of the Literature" (The Journal of TRAUMA, vol. 53, No. 3) pp. 549-552, Sep. 2002.
Hideki Mizu-uchi et al., "The Effect of Ankle Rotation on Cutting of the Tibia in Total Knee Arthroplasty" (The Journal of Bone & Joint Surgery), Dec. 2006, 88:2632-2636.

* cited by examiner

*Primary Examiner* — Jerry Cumberledge
*Assistant Examiner* — Nicholas Plionis
(74) *Attorney, Agent, or Firm* — Lerner, David, Littenberg, Krumholz & Mentlik, LLP

(57) ABSTRACT

A method for implanting a longitudinal intramedullary nail into the tibia comprises inserting the tibia nail along a plane of symmetry through the tuberositas tibiae. Thereby, the tuberositas tibiae can be used during nail insertion to correctly align the nail and the target arm to the symmetry plane of the bone. This means, that the whole construct, the nail attached to the target arm, has to be inserted in external rotation.

20 Claims, 4 Drawing Sheets

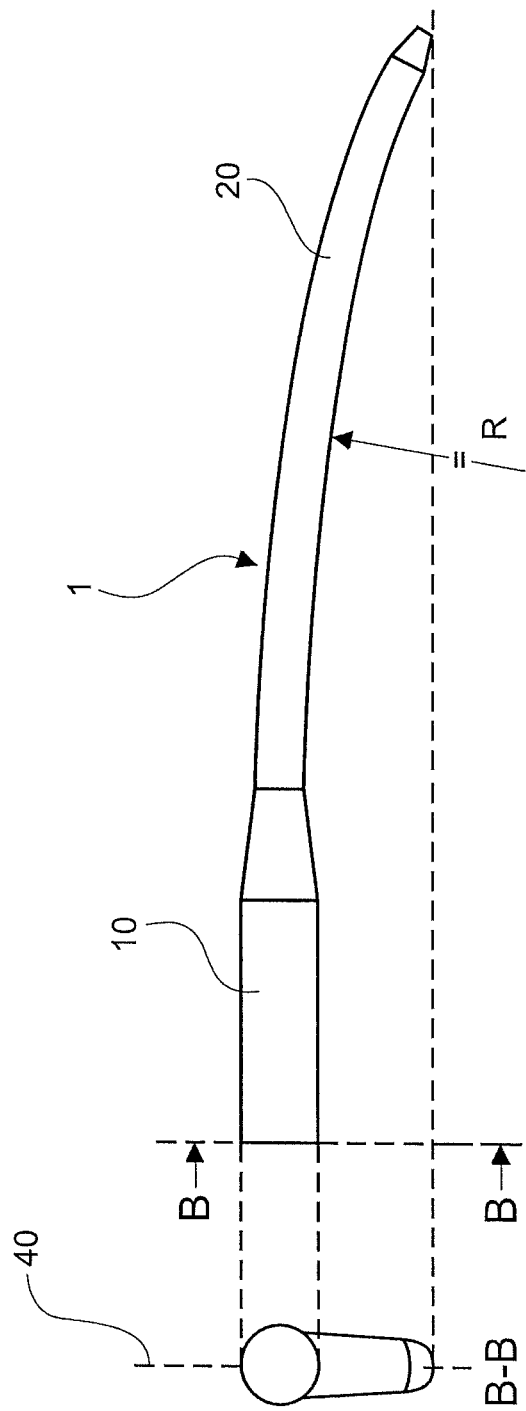

METHOD FOR TIBIAL NAIL INSERTION

BACKGROUND OF THE INVENTION

The invention generally relates to methods for tibial nail insertion. In particular, the invention relates to a method for implanting a longitudinal intramedullary nail into a tibia.

Tibial nailing often requires intensive hammering during insertion which might cause iatrogenic fractures.

Getting the rotation correct after intramedullary nailing is a clinical challenge, especially for the femur. However, tibial malrotation after intramedullary nailing is likely more common than reported. The cases of three patients who incurred symptomatic rotational deformities after closed intramedullary nailing are reported in Kevin M. Kahn, M D, et al. "Malrotation after locked intramedullary tibial nailing: Three case reports and review of the literature" (The Journal of TRAUMA, Vol. 53, Number 3, pages 549 to 552). Today, the rotation of a fractured tibia is compared to its non-fractured counterpart, respectively. The rotation is generally evaluated measuring the difference in torsion. The range of acceptable malrotation may be less than 15 degrees.

However, the shape of the tibia is unique. The tibia may have a rotational mismatch between its proximal and distal ends and the ankle joint is externally rotated relative to the proximal part of the tibia (Hideki Mizu-uchi et al. "The effect of ankle rotation on cutting of the tibia in total knee arthroplasty" (The Journal of Bone & Joint Surgery 2006; 88:2632-2636)).

For a better understanding, it is noted that the proximal end of the bone is the end of the bone being oriented toward the heart of the human body. The distal end of the bone is the end of the bone being oriented away from the heart of the human body. An intramedullary nail may be a tibia nail, wherein the intramedullary nail comprises a non-driving end and a driving end. The non-driving end is the end of the nail which firstly enters the intramedullary channel of a bone. Entering a bone from the proximal end of the bone is denoted as antegrade entering. Entering a bone from the distal end of the bone is denoted as retrograde entering. Consequently, a nail adapted to be implanted from the proximal end of the tibia may be denoted as antegrade tibial nail.

A tuberositas tibiae plane is a plane defined by the tuberositas tibiae, i.e. the tip most protruding to the front at the proximal end of the tibia, the entry point into the medullary channel and the axis of the medullary channel inside the tibia. Furthermore, the sagittal plane related to the tibia means a vertical plane orientated from the front to the back (anteroposterior) in a natural position of the leg relative to the chest of a human, for example when the lower leg is tensionlessly placed on a table surface with the toes orientated upwardly. Accordingly, the tuberositas tibiae plane is slightly inclined, i.e. externally rotated approximately between 13 degrees and 37 degrees relative to the sagittal plane.

BRIEF SUMMARY OF THE INVENTION

A smoother nail design with obtuse bends or even curvatures instead of acute-angled bends may provide improved insertion characteristics, avoid hammering and thus improve the clinical outcome.

Trying to understand the anatomy of the tibia is the key to facilitate the nailing procedure and optimize the surgical technique. None of the common three anatomical planes, not even the sagittal plane, can be used to divide the tibia into two symmetric halves.

In morphologic investigations with regard to distinctive landmarks, a tuberositas tibiae plane, that is a natural symmetry plane of the tibia has been identified. The cross section around the diaphysis forms an irregular triangle. The symmetry plane runs through the triangle's cone end represented by the tuberositas tibiae (TT) and it's elevated continuation to the distal part.

The idea is to insert tibia nails along the described tuberositas tibiae plane. Thereby, the tuberositas tibiae can be used during nail insertion to correctly align the plane of the nail containing the radius of the curved nail portion and the target arm to the symmetry plane of the bone. This means, that the whole construct, the nail attached to the target arm, has to be inserted in external rotation.

In a further study, it has been determined that a nail with a retro-curved axis, a constant radius of curvature would optimally fit the medullary canal, if the nail is inserted according to the above-described procedure. This radius of curvature in the natural symmetry plane of the tibia extends between 2000 mm and 3000 mm (preferably 2500 mm). Either a constant radius or any approximation (due to straight driving and non-driving ends with tangential connections to the curved part) within the given radius of curvature range would fit the medioposterior curvature of the tibia.

In summary, nailing the tibia along its medioposterior symmetry plane will offer the following benefits:

1) The approach permits not only a design for a dedicated left and a dedicated right nail, but also a universal design for combined left and right nails with an either constant retro-curved radius or a smooth connection between the established Herzog bend of the nail, its shaft and possible distal bend. The smooth design in turn may improve the insertion characteristics significantly, avoid intensive hammering and iatrogenic fractures which remains to be verified.
2) Owing to the triangular shaped tibia shaft, drilling for all proximal and distal mediolateral screws will be carried out more perpendicular to the medial cortex preventing sliding of the drill.
3) Additionally, the drilling and locking procedure will be simplified for the surgeon due to the laterally orientated target arm and thus the external dislocation of the operating field with better accessibility.
4) In case of a universal nail design for a combined left and right nail, all screws in the tibial plateau have to be placed symmetric to the longitudinal nail axis at an angle of between 40 and 50 degrees, preferably a 45 degrees angle between both proximal screws and symmetric plane, in order to guarantee that their tips penetrate the cortex in equivalent spots but at slightly different heights if the whole construct is rotated left and right. These new screw trajectories in the tibial plateau also reduce the risk of penetrating the tibiofibular joint.
5) Furthermore, this principle is considered to be used for control, restoration and adjustment of the correct rotation. Obviously, there seems to be a dependency between the natural rotation of the ankle and the natural symmetry plane of the tibia defined by the tuberositas tibiae. The idea is to use this correlation to control the rotation. This landmark-based approach, i.e. orienting the tuberositas tibia to the natural external rotation of the ankle during fracture reduction, is not geared to the healthy contra lateral side and will potentially be more accurate, reduce operation room time and thus improve the clinical outcome. The technique of the present invention is thus not geared to the healthy contra lateral side and will potentially be more accurate, reduce operation room time and thus improve the clinical outcome.

According to a first embodiment of the invention, a method for implanting a longitudinal intramedullary nail into the tibia, comprises the steps of providing a longitudinal intramedullary nail having a section with a curvature, which curvature has a predetermined radius; identifying the tuberositas tibiae plane; aligning the intramedullary nail, such that the radius of the intramedullary nail lies in the tuberositas tibiae plane; and inserting the intramedullary nail into a marrow (medullary) channel of the tibia.

According to an embodiment of the invention, the intramedullary nail is an intramedullary tibia nail. According to another embodiment of the invention, the radius of the nail is between 2000 mm and 3000 mm. The radius may also be between 2400 mm and 2600 mm. Furthermore, the radius may be about 2500 mm.

The curvature of the intramedullary nail section may correspond to a curvature of the marrow channel of the tibia into which the intramedullary nail is to be inserted.

Accordingly, it depends on the actual anatomy of the fractured tibia what radius of the tibia nail should be preferred.

According to a further embodiment of the invention, the method further comprises the step of placing screws in a tibia plateau at the proximal end of a tibia into which the intramedullary nail is to be inserted in an angle of for example 40 degrees to 50 degrees, depending on the actual position and orientation of transverse holes in the proximal portion of the intramedullary nail.

According to a second embodiment of the invention, a method for implanting a longitudinal intramedullary nail into the tibia, comprises providing a longitudinal intramedullary nail having a section with a curvature, which curvature has a predetermined radius; identifying a sagittal plane of the tibia; aligning the intramedullary nail, such that the radius of the intramedullary nail lies in a plane being inclined externally rotated by an angle between 13 degrees to 37 degrees with respect to the sagittal plane of the tibia; and inserting the intramedullary nail into a marrow (medullary) channel of the tibia, wherein the intramedullary nail may be an intramedullary tibia nail.

According to an embodiment of the invention, the angle is between 17 degrees and 33 degrees. The angle may also be between 21 degrees and 26 degrees. Furthermore, the angle may be about 24 degrees. It will be understood, that the angle of rotation differs due to the actual anatomy of a specific tibia.

The curvature of the intramedullary nail section may correspond to a curvature of the marrow channel of the tibia into which the intramedullary nail is to be inserted.

Also with respect to this aspect of the invention, the radius may be between 2000 mm and 3000 mm. The radius may also be between 2400 mm and 2600 mm. Furthermore, the radius maybe about 2500 mm.

According to an embodiment of the invention, the method further comprises the step of placing screws in a tibial plateau of a tibia into which the intramedullary nail is to be inserted in an angle of for example 40 degrees to 50 degrees, depending on the actual position and orientation of transverse holes in the proximal portion of the intramedullary nail.

These aspects defined above and further aspects, features and advantages of the present invention can also be derived from the examples of the embodiments to be described hereinafter and are explained with reference to the examples of the embodiments to which the invention is not limited.

BRIEF DESCRIPTION OF THE DRAWINGS

The invention will now be detailed by way of exemplary embodiments with reference to the attached drawings.

FIG. 6 is a side view of a tibia nail according to the invention.

FIG. 7 is a front view of a tibia nail according to the invention.

It is noted that the illustration of the drawings is only schematically and not to scale. In different figures, similar elements are provided with the same reference signs.

DETAILED DESCRIPTION

In the following, FIGS. 1 to 5 are described illustrating specific anatomic aspects of a tibia and orientations of these aspects at a tibia, relevant for the understanding of the invention.

Figures 1, 2, 3:
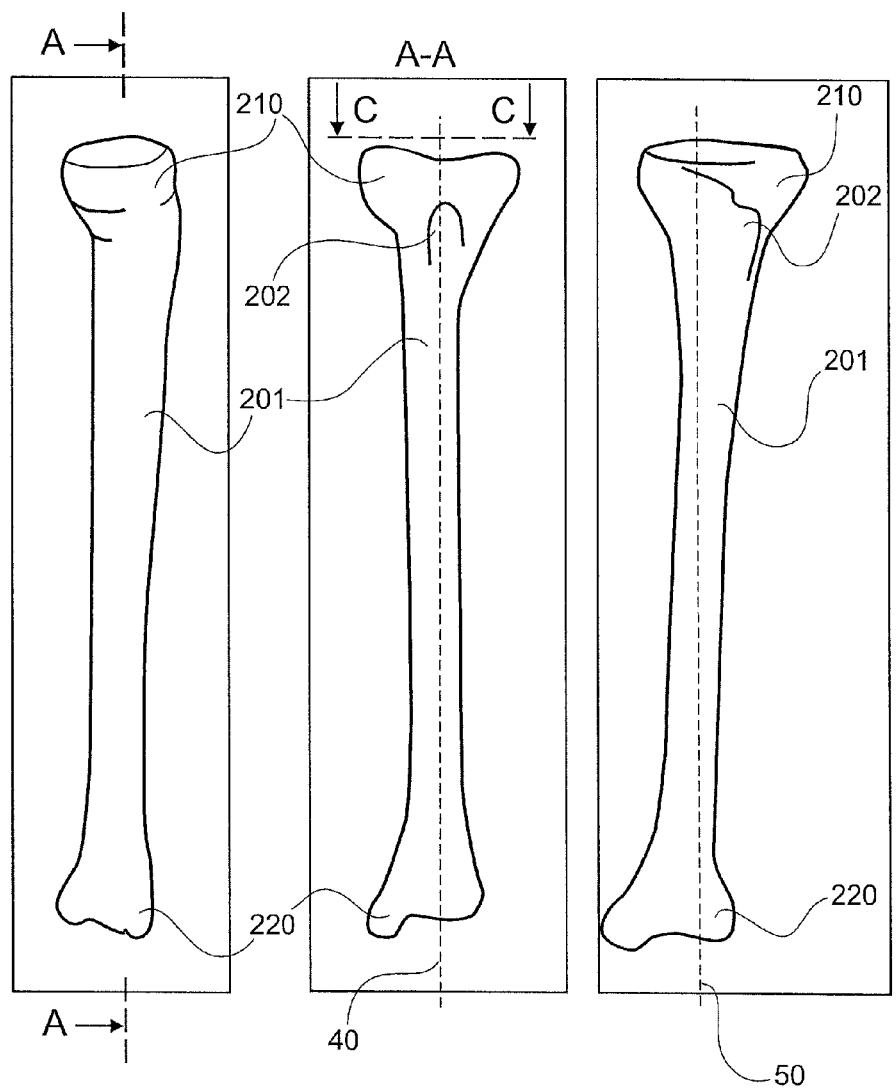
FIG. 1 shows an example of a left tibia viewed in a lateral to medial direction.
FIG. 2 shows a left tibia with a tuberositas tibiae plane perpendicular to the drawing sheet.
FIG. 3 shows a left tibia with a sagittal plane perpendicular to the drawing sheet.

FIG. 1 shows the outer contour of a tibia bone 201 with a proximal end 210 of the tibia and a distal end 220 of the tibia. The tibia in FIG. 1 is shown substantially from a medio-lateral direction.

As indicated by the arrows A-A in FIG. 1, the tibia in FIG. 2 is shown substantially from the front (anterior), wherein the tibia 201, in this view, includes a tuberositas tibiae 202. Furthermore, the tuberositas tibiae plane 40 extending through the tuberositas tibiae 202 is indicated in FIG. 2.

In FIG. 3 the tibia is shown together with a sagittal plane 50. The tibia 201 includes proximal end 210, tuberositas tibiae 202, and distal end 220.

Figures 4, 5:
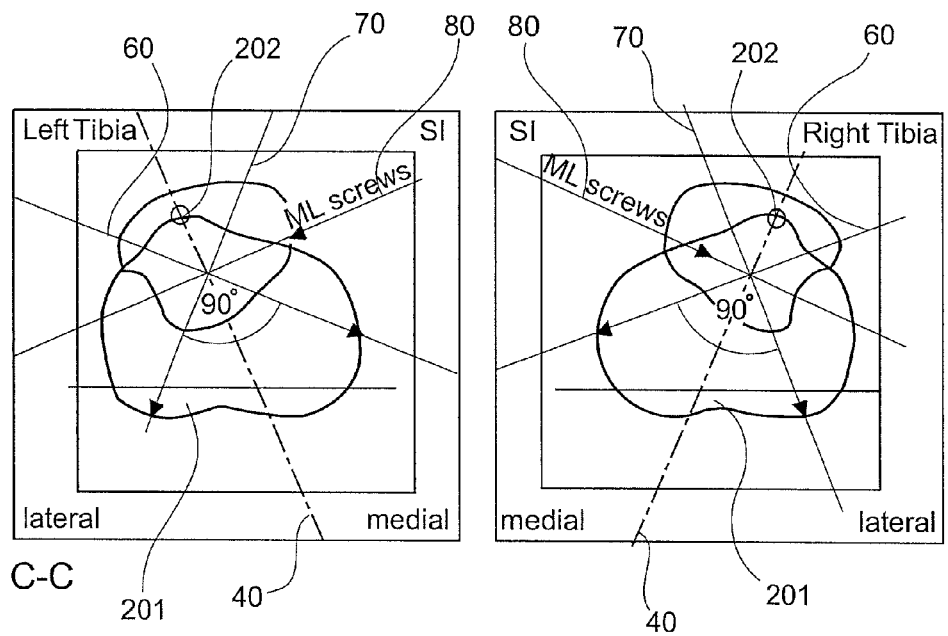
FIG. 4 shows a top view of a proximal end of a left tibia.
FIG. 5 shows a top view of a proximal end of a right tibia.

FIG. 4 is a view in the direction C-C (as indicated in FIG. 2), i.e. a top view on the proximal end of a left tibia. FIG. 5 is a top view on the proximal end of a right tibia. In both figures, the tuberositas tibiae plane 40 is shown extending through tuberositas tibiae 202. Furthermore, possible screw insertion directions 60, 70 for locking screws to be introduced into the proximal end of an intramedullary nail are shown. Furthermore, a screw insertion direction 80 for a medio-lateral (ML) screw is shown. A second screw 80a may be inserted in the ML direction which is parallel to direction 80.

FIGS. 6 and 7 are views of an intramedullary nail, i.e. of a tibia nail, in accordance with the invention. The tibia nail 1 includes a proximal end portion 10 and a distal end portion 20, wherein the distal end portion 20 is curved with a radius R. The curvature along the central axis of the nail lies in a single plane. In FIG. 7, the tuberositas tibiae plane 40 is additionally shown. It can be seen from FIGS. 6 and 7, that the curvature of the nail is formed within one plane. The radius R is between 2000 and 3000 mm.

Figures 8, 9:
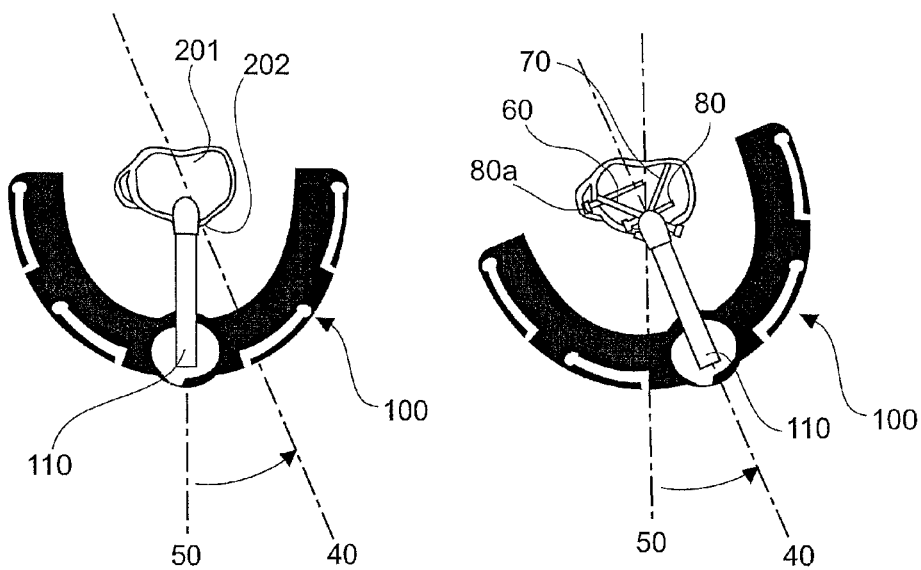
FIG. 8 is a top view of a target arm relative to a tibia plateau.
FIG. 9 is a top view is the rating an orientation of a target arm during an insertion according to the invention.

FIGS. 8 and 9 show a tibia 201 together with a targeting device 100 comprising a targeting arm 110. In FIG. 8, targeting arm 110 is orientated parallel to a sagittal plane 50 of the tibia. Closely beside an end 52 of the targeting arm, the tuberositas tibiae 202 is visible. In FIG. 9, the targeting arm 110 of the targeting device 100 is rotated about the angle $\alpha$ so that the targeting arm is now orientated parallel to the tuberositas tibiae plane 40. With the targeting device in an orientation relative to the tibia as shown in FIG. 9, a tibia nail may be introduced into the medullary channel of the tibia, in accordance with the invention.

Further shown in FIG. 9 are locking screws, two of which orientated in a medio-lateral direction, denoted with reference sign 80. Further screws may be introduced inclined with respect to that direction, wherein these further screws may be orientated perpendicular relative to each other, as indicated in FIGS. 4 and 5.

Figure 10:
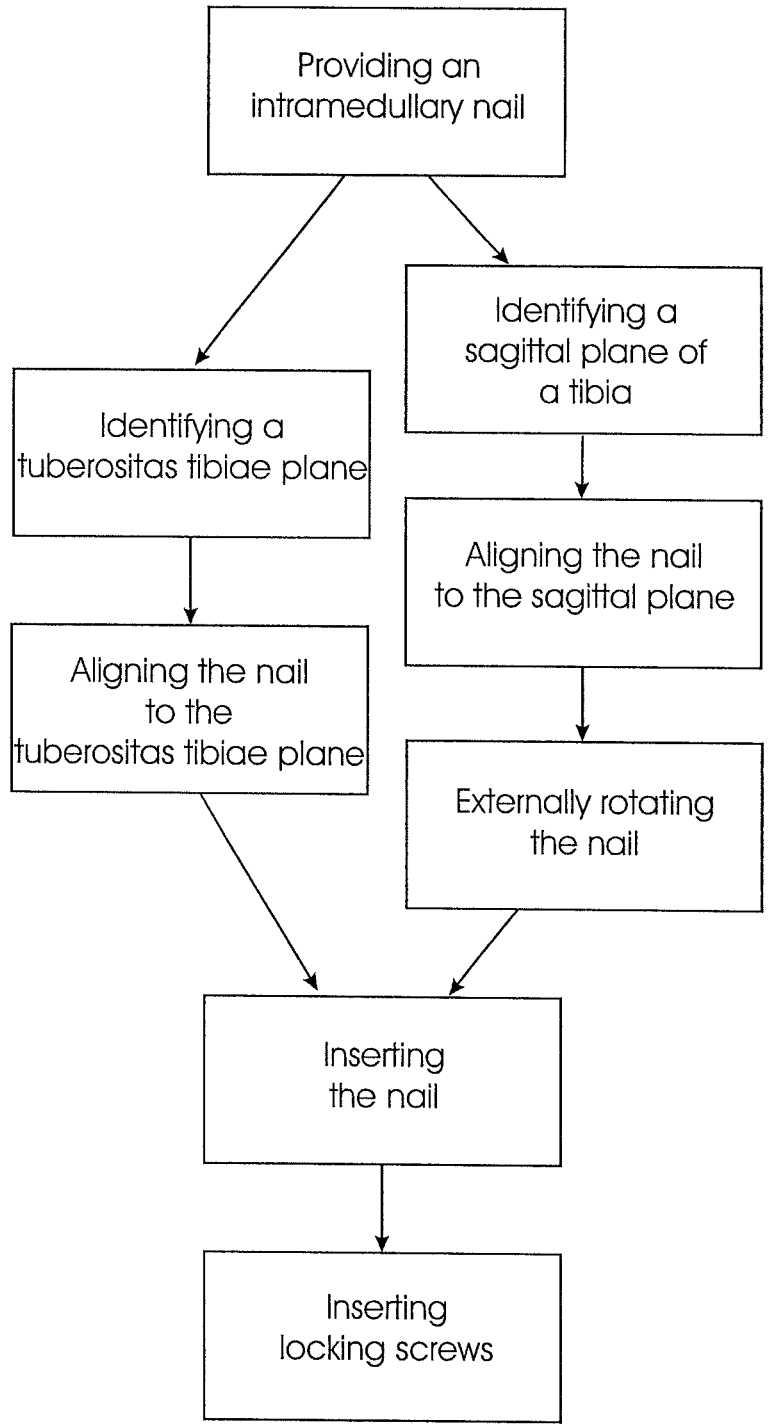
FIG. 10 is a flowchart of embodiments of a method according to the invention.

The flowchart in FIG. 10 illustrates the principle of the steps performed in accordance with the invention. It will be understood that the steps described, are major steps, wherein these major steps might be differentiated or divided into several sub-steps. Furthermore, there might be also sub-steps between these major steps. Therefore, a sub-step is only mentioned if this step may be important for the understanding of the principles of the method according to the invention.

In a first step, a longitudinal intramedullary nail 1 having a curved section is provided wherein the curvature has a predetermined radius as discussed above.

In a next step, in accordance with a first embodiment of the invention, the tuberositas tibiae plane is identified. This identification is performed by firstly identifying the tuberositas tibiae and the entry point into the medullary channel on the upper surface of the tibia, and secondly by identifying the axis of the medullary channel. The tuberositas tibiae, the entry point as well as the axis of the medullary channel lie on the tuberositas tibiae plane.

The intramedullary nail is aligned in a following step, such that the radius of the curved section of the intramedullary nail lies in the tuberositas tibiae plane.

Alternatively, in accordance with a second embodiment of the invention, a sagittal plane of the tibia is identified.

Then, the intramedullary nail is firstly aligned with the sagittal plane, i.e. the radius of the intramedullary nail lies in the sagittal plane, and secondly is externally rotated by an angle between 13 degrees to 37 degrees with respect to the sagittal plane orientation of the tibia previously determined.

In a subsequent step, the intramedullary nail is inserted into a marrow channel of the tibia through an entry point in the tibial plateau.

Finally, screws may further be placed in a tibia plateau of the tibia into which the intramedullary nail is to be inserted. The actual position and orientation of each screw depends on the actual design of the driving end portion of the intramedullary nail. Finally, further locking screws are inserted through transverse bores in the non-driving end portion of the nail, so that the distal portion of the tibia may be reliably fixed relative to the proximal portion of the tibia.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited and mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for implanting a longitudinal intramedullary nail into a tibia, the method comprises:
    providing a longitudinal intramedullary nail having a section with a curvature, which curvature has a predetermined radius lying along a plane containing the longitudinal axis of the nail;
    identifying a plane of symmetry through a tuberositas tibiae;
    wherein the tuberositas tibiae, an entry point into a marrow channel and a longitudinal axis of the marrow channel all lie on the plane of symmetry through the tuberositas tibiae;
    aligning the intramedullary nail, such that the plane containing the radius of the intramedullary nail section lies in the plane of symmetry through to the tuberositas tibiae; and
    inserting the intramedullary nail into the marrow channel of the tibia.

2. The method of claim 1, wherein the radius is between 2000 mm and 3000 mm.

3. The method of claim 1, wherein the radius is between 2400 mm and 2600 mm.

4. The method of claim 1, wherein the radius is about 2500 mm.

5. The method of claim 1, wherein the curvature of the intramedullary nail section corresponds to a curvature of the marrow channel of the tibia into which the intramedullary nail is to be inserted.

6. The method of claim 1, further comprising placing two screws in a tibia plateau of the tibia into which the intramedullary nail is to be inserted at an angle of 40° to 50° with respect to the plane through the tuberositas tibiae.

7. The method of claim 6 wherein a further two screws are inserted in parallel into a proximal portion of the tibia in a medial-lateral direction.

8. A method of implanting an intramedullary nail in a tibia comprising:
    providing a longitudinally extending intramedullary nail having an axially extending curved portion with a center and a radius lying in a plane extending through a longitudinal axis of the nail curved portion;
    identifying a plane of symmetry extending through a tuberositas tibiae of the tibia and through a medullary canal of the tibia;
    inserting the nail into the medullary canal with the plane containing the radius of the intramedullary nail curved portion coplanar with the plane of symmetry through the tuberositas tibiae.

9. The method as set forth in claim 8 further comprising inserting a screw in a proximal portion of the tibia in a direction oriented at 40 to 50° to the plane containing the nail radius.

10. The method as set forth in claim 9 further comprising inserting a screw in the proximal portion of the tibia in a direction perpendicular to the plane containing the nail radius.

11. A method for implanting a longitudinal intramedullary nail into a tibia, the method comprises:
    providing a longitudinal intramedullary nail having a section with a curvature, which curvature has a predetermined radius lying in a plane containing a longitudinal axis of the nail section with a curvature;

identifying a tuberositas tibiae plane of symmetry by identifying a tuberositas tibiae and an entry point into the marrow channel on an upper surface of the tibia and identifying a longitudial axis of the marrow channel;

aligning the intramedullary nail, such that the plane containing the radius of the intramedullary nail lies in the tuberositas tibiae plane of symmetry; and inserting the intramedullary nail into the marrow channel of the tibia.

12. The method of claim 11, wherein the tuberositas tibiae, the entry point into the marrow channel and a longitudinal axis of the marrow channel lie on the tuberositas tibiae plane.

13. The method of claim 11, wherein the radius is between 2000 mm and 3000 mm.

14. The method of claim 11, wherein the radius is between 2400 mm and 2600 mm.

15. The method of claim 11, wherein the radius is about 2500 mm.

16. The method of claim 11, wherein the curvature of the intramedullary nail section corresponds to a curvature of the marrow channel of the tibia into which the intramedullary nail is to be inserted.

17. The method of claim 11, further comprising placing two screws in a tibia plateau of the tibia into which the intramedullary nail is to be inserted at an angle of 40° to 50° to the tuberositas tibiae plane.

18. The method of claim 17 wherein a further two screws are inserted in parallel into a proximal portion of the tibia in a medial-lateral direction.

19. A method for implanting a longitudinal intramedullary nail into a tibia, the method comprises:

providing a longitudinal intramedullary nail having a section with a curvature, which curvature has a predetermined radius lying along a plane containing a longitudinal axis of the nail in the section with the curvature;

identifying a plane through a tuberositas tibiae that defines a proximal tibial medial-lateral symmetry;

aligning the intramedullary nail, such that the plane containing the radius of the intramedullary nail section with the curvature is coplanar with the tuberositas tibiae symmetry plane; and inserting the intramedullary nail into a marrow channel of the tibia.

20. The method of claim 19, wherein the tuberositas tibiae, an entry point into the marrow channel and a longitudinal axis of the marrow channel all lie on the tuberositas tibiae symmetry plane.

* * * * *